(12) United States Patent
Tempere

(10) Patent No.: US 6,447,253 B2
(45) Date of Patent: Sep. 10, 2002

(54) TURBINE ROTOR DISK FITTED WITH BLADES HAVING CHRISTMASTREE-SHAPED ROOTS, AND A METHOD OF MOUNTING A BLADE ON A DISK

(75) Inventor: Robert Tempere, Aulnay sous Bois (FR)

(73) Assignee: Alstom Power N.V., Amsterdam (NL)

( * ) Notice: Subject to any disclaimer, the term of this patent is extended or adjusted under 35 U.S.C. 154(b) by 0 days.

(21) Appl. No.: 09/774,605

(22) Filed: Feb. 1, 2001

(30) Foreign Application Priority Data

Mar. 30, 2000 (FR) .......................................... 00 04078

(51) Int. Cl.[7] ................................................. B63H 1/20
(52) U.S. Cl. ...................................................... 416/221
(58) Field of Search ............................ 416/221, 220 R, 416/206, 500

(56) References Cited

U.S. PATENT DOCUMENTS

| | | | |
|---|---|---|---|
| 4,022,545 A | * 5/1977 | Shank | 416/221 |
| 5,123,813 A | * 6/1992 | Przytulski et al. | 416/221 |
| 5,160,243 A | * 11/1992 | Herzner et al. | 416/220 R |
| 5,236,309 A | * 8/1993 | Van Heusden et al. | 416/221 |
| 5,240,375 A | * 8/1993 | Wayte | 416/219 R |
| 5,431,543 A | * 7/1995 | Brown et al. | 416/221 |
| 6,102,664 A | * 8/2000 | Nguyen | 416/248 |

* cited by examiner

*Primary Examiner*—Edward K. Look
*Assistant Examiner*—James M McAleenan
(74) *Attorney, Agent, or Firm*—Sughrue Mion, PLLC

(57) ABSTRACT

A turbine rotor disk fitted with blades having Christmastree-shaped roots, said disk having complementary slots each receiving the root of a blade, wherein at least one stick having a setback holding a spring strip captive is placed in the bottom of each slot of the disk between said bottom and the end face of the root of the corresponding blade. During assembly, the slot of the disk corresponding to the blade that is to be mounted is put in the bottom position and then the root of the blade to be mounted is slid into the slot, after which the sticks, each fitted with its own spring strip are inserted in succession into the empty space between the bottom of the slot and the end of the root of the blade.

8 Claims, 5 Drawing Sheets

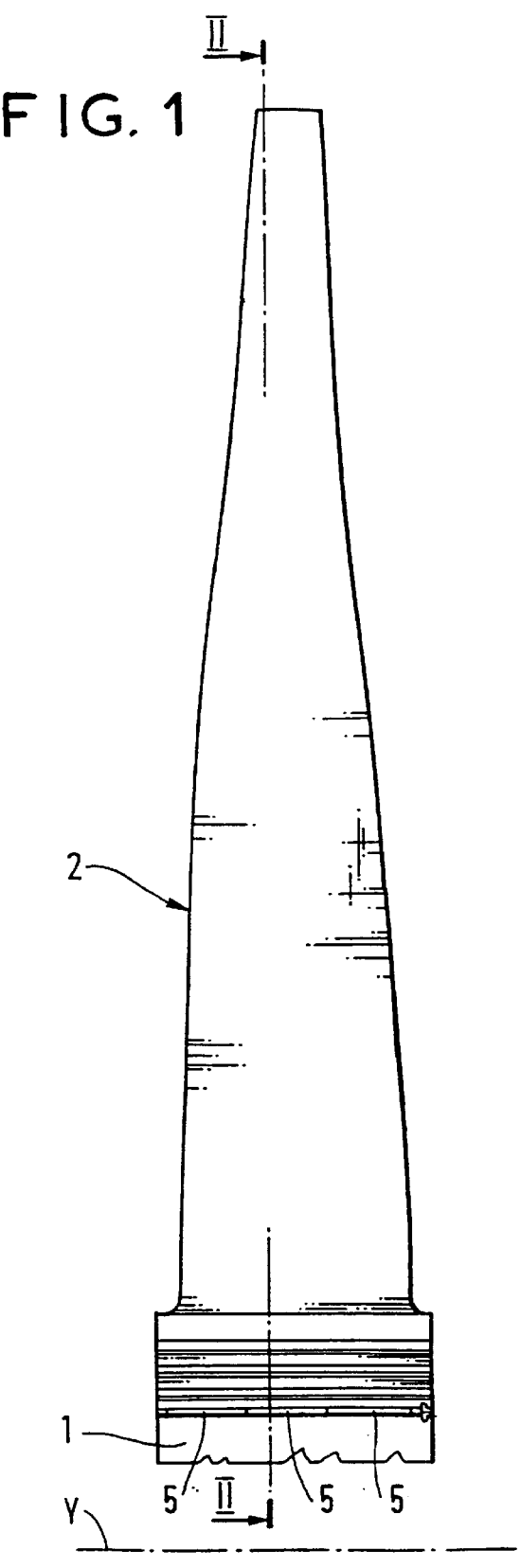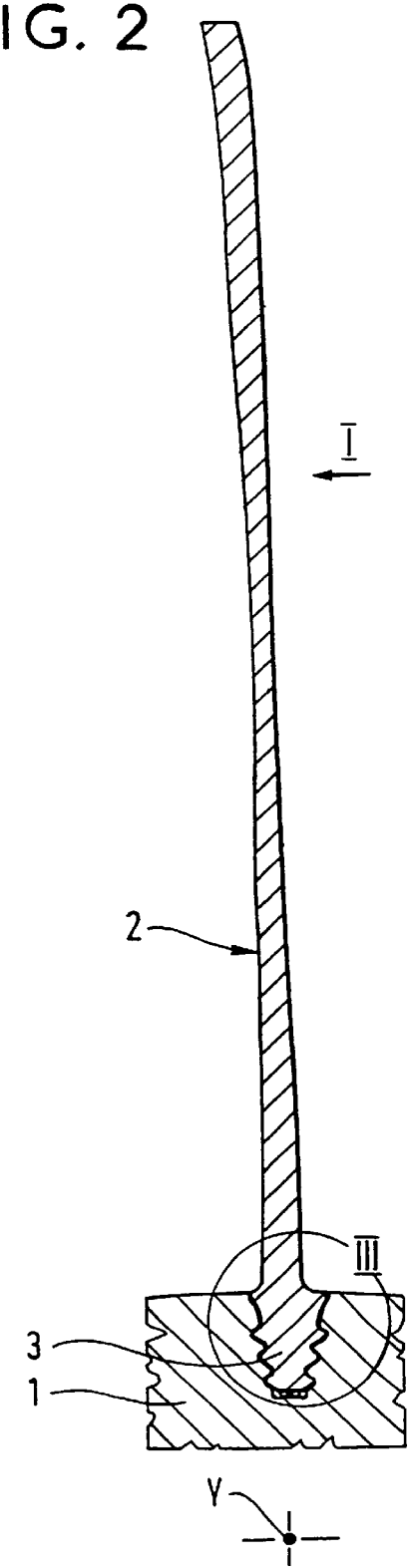

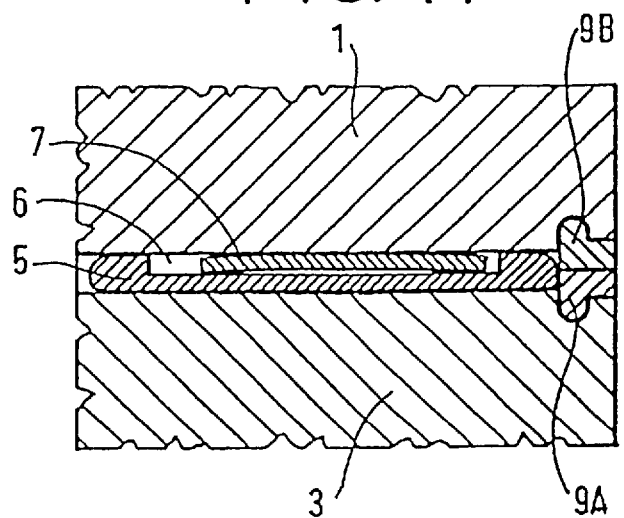
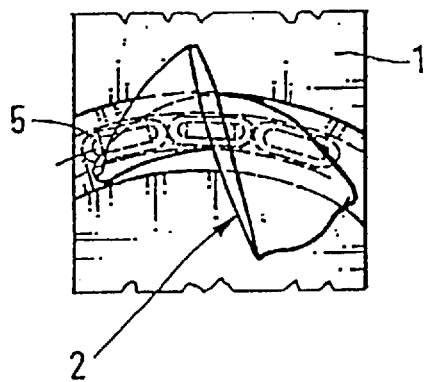
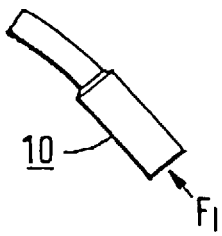
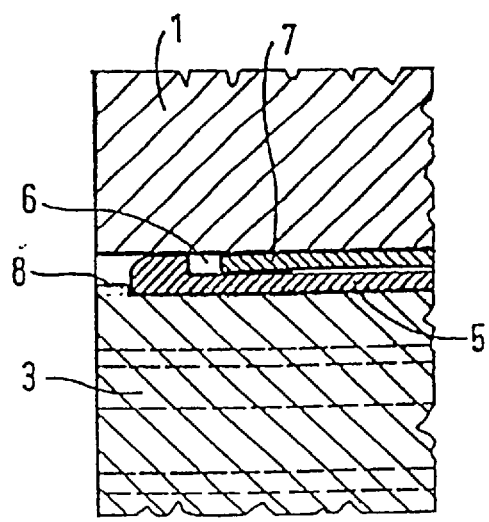
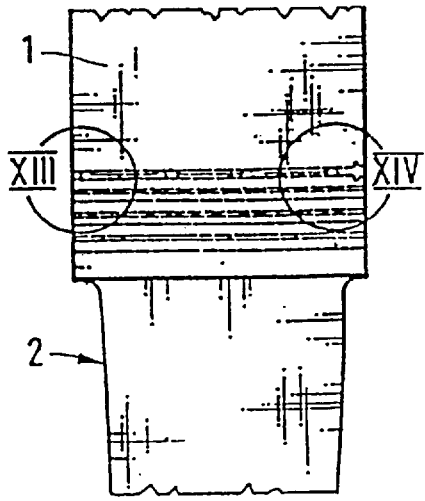

US 6,447,253 B2

TURBINE ROTOR DISK FITTED WITH BLADES HAVING CHRISTMASTREE-SHAPED ROOTS, AND A METHOD OF MOUNTING A BLADE ON A DISK

The present invention relates to a turbine rotor disk fitted with blades having Christmastree-shaped roots.

More particularly, the invention relates to means enabling blades having Christmastree-shaped roots to be properly secured to the disk on which they are mounted, even at slow speeds of rotation.

BACKGROUND OF THE INVENTION

With this method of fixing where the root of each blade is said to be "Christmastree-shaped" and is received in a complementary slot in the rotor disk on which the blades are mounted, it is necessary for rotation to be taking place at sufficient speed before centrifugal force ensures that no relative movement is possible. The teeth on the root of the blade do not bear properly against the corresponding grooves in a slot of the disk at low speeds, and a known remedy to this drawback is to provide a few setbacks, generally three setbacks, in the end face of the root to provide housings for receiving springs.

Each spring is constituted by a single curved strip placed in a setback: the ends of the strip are in the setback and the curved portion is directed outwardly, i.e. against the bottom of the corresponding slot in the rotor disk. Naturally, the depth of the setback is smaller than the deflection in the middle of the curved spring.

When the blades are mounted on the disk, the springs are placed in their setbacks and the Christmastree-shaped rotor of each blade is inserted into the corresponding slot of the disk, i.e. simultaneously with its three springs. This operation is very difficult and accidents often arise such as springs breaking or jamming.

OBJECTS AND SUMMARY OF THE INVENTION

An object of the present invention is to provide a turbine rotor disk fitted with blades having Christmastree-shaped roots, where the teeth of the blade roots are pressed against the complementary grooves formed in the slots of the disk by springs while avoiding the above-mentioned drawbacks of the prior art during assembly.

The invention thus provides a turbine rotor disk fitted with blades having Christmastree-shaped roots, said disk having complementary slots each receiving the root of a blade, wherein at least one stick having a setback holding a spring strip captive is placed in the bottom of each slot of the disk between said bottom and the end face of the root of the corresponding blade.

Advantageously, three of said sticks are disposed between the bottom of a slot in the disk and the end face of the root of the corresponding blade.

According to another characteristic, the end of the root of each blade has a rim against which one of said sticks comes into abutment.

The invention also provides a method of assembling a blade having a Christmastree-shaped root to a turbine rotor disk of the invention, the method comprising the following sequence of operations:

a) the rotor disk is placed so that its axis is in a horizontal position;
b) the slot of the disk in which the blade root is to be mounted is placed in the bottom position;
c) the blade is installed by slidably inserting the root of the blade in the slot of the disk; and
d) the stick(s) each fitted with a respective spring strip are then inserted into the empty space between the bottom of the slot in the disk and the end of the blade root until the first-inserted stick comes into abutment against said rim on the root of the blade.

BRIEF DESCRIPTION OF THE DRAWINGS

An embodiment of the invention is described below with reference to the accompanying drawings, in which:

FIG. 1 is a fragmentary view of a steam turbine rotor disk of the invention seen looking along arrow I of FIG. 2;

FIG. 2 is a section view on II—II of FIG. 1;

FIGS. 11 and 12 are similar to FIGS. 7 and 8 but after a blade has been installed;

FIG. 13 is an enlargement of a detail XIII of FIG. 11;

FIG. 14 is an enlargement of a detail XIV of FIG. 11; and

FIG. 15 shows a tool used for inserting sticks in their locations.

MORE DETAILED DESCRIPTION

Figure 3:
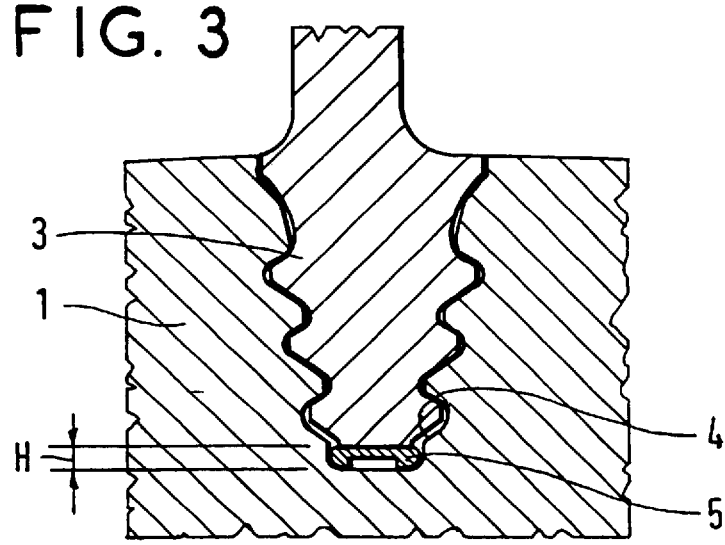
FIG. 3 is an enlargement of fragment III of FIG. 2.

With reference to FIGS. 1 to 3, there can be seen a small part of a steam turbine rotor disk 1 having a blade 2 mounted thereon.

The blade has a root which is said to be "Christmastree-shaped". This is the base 3 of the blade whose general shape when seen in section perpendicular to the axis Y of the rotor disk resembles a Christmas tree. This Christmastree-shaped root 3 serves to secure the blade 2 relative to the disk 1. The root 3 is inserted in a corresponding slot 4 of the disk 1.

In the invention, and as can be seen in the detail III shown on a larger scale in FIG. 3, a stick 5 is placed between the bottom of the slot 4 and the end of the root 3 of the blade 2. In practice, three of these sticks are inserted one after another: they are referenced in FIG. 1.

Figure 4:
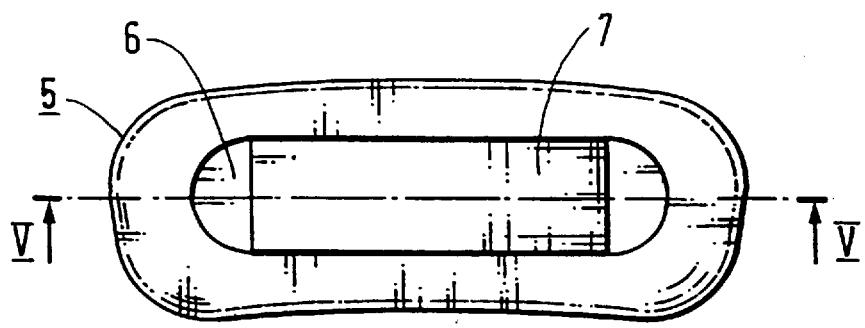
FIGS. 4 and 5 are respectively a plan view and a section view on V—V of FIG. 4 showing a stick used for mounting a blade on the rotor disk.
Figure 5:
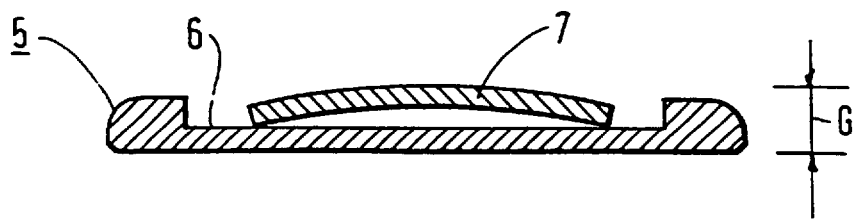

Each stick is fitted with a spring strip (not shown in FIGS. 1 to 3), but visible in the stick shown on its own in FIGS. 4 and 5. As can be seen in these figures, the stick 5 has a setback 6 in which a spring strip 7 is placed and held captive.

In FIGS. 11 and 12, the blade 2 can be seen mounted on the disk 1. FIG. 11 corresponds to FIG. 1 after the disk has turned so as to place the blade 2 pointing downwards, and FIG. 12 is a view seen along arrow XII of FIG. 11.

The detail referenced XIII in FIG. 11 and shown on a larger scale in FIG. 13 shows that the end of the Christmastree-shaped root 3 of the blade 2 has a rim 8 against which the first stick 5 to be inserted comes into abutment.

Detail XIV of FIG. 11, shown on a larger scale in FIG. 14, shows the other face of the disk 1 where the series of blades 2, all mounted in the same manner as explained above, is closed laterally in conventional manner by a two-part ring 9A, 9B made up of a plurality of segments that are subsequently bonded together.

As can be seen in the detail shown in FIG. 3, the empty space between the end of the root 3 and the bottom of the slot 4 in the disk 1 is of height H.

In FIG. 5 which shows the stick 5 in isolation together with its spring strip 7 (which spring is merely a curved spring strip), the total height of the stick plus its spring at rest is equal to G and naturally, the height G is greater than H so that the spring can perform its function of pressing the roots of the blades against the grooves in the slots of the disk.

As shown in FIG. 5, the ends of the spring strip 7 are in the bottom of the setback 6 while the curved portion in the middle is pressed against the bottom of the slot 4 in the rotor disk 1 once the stick 5 has been inserted between the root of the blade and the bottom of the slot, with the plane face of the stick 5 then bearing against the end of the root 3 of the blade (see FIGS. 3, 13, and 14).

FIGS. 6 to 10 show how a blade 2 is mounted on the rotor disk 1.

Figure 6:
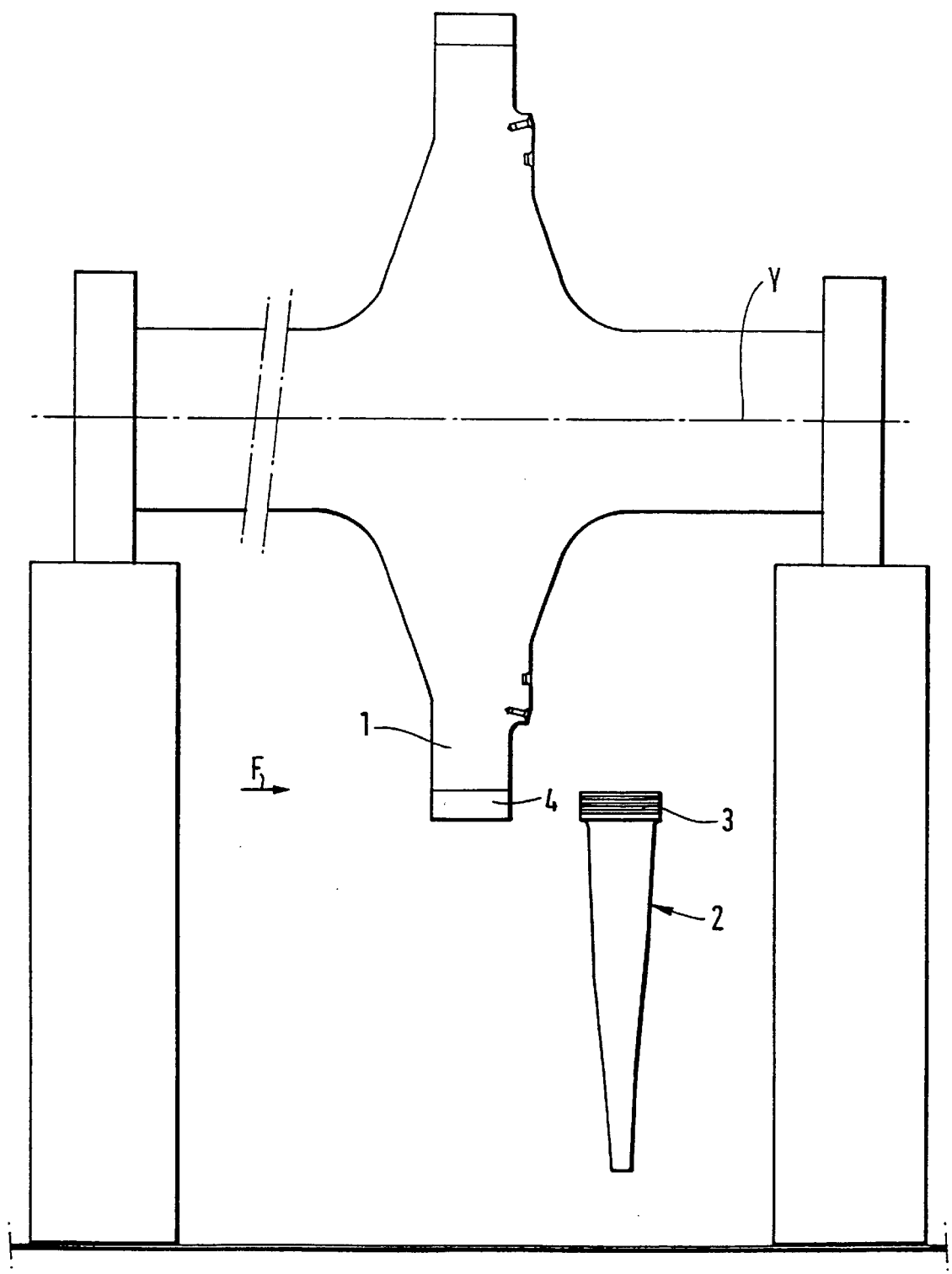
FIG. 6 is a fragmentary diagrammatic view of a turbine rotor in which there can be seen a disk with a blade in position to be assembled.
Figure 7:
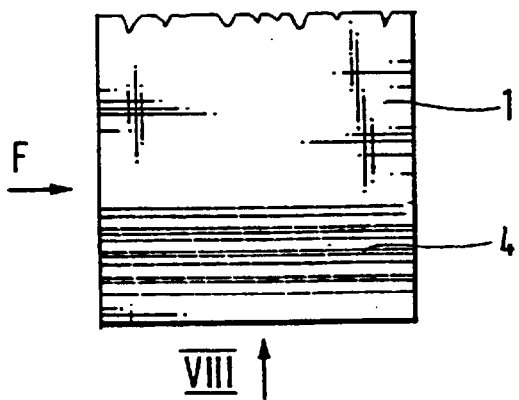
FIG. 7 shows a fragment of the disk with a slot in the low position.
Figure 9:
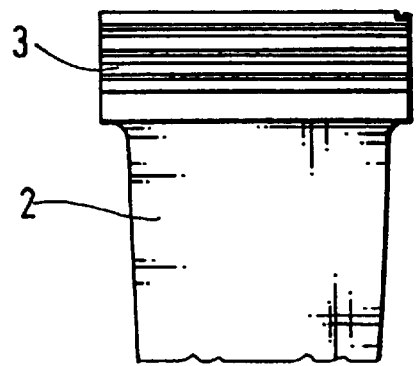
FIG. 9 shows a blade in position to be assembled in the rotor disk slot shown in FIGS. 7 and 8.

As shown in FIG. 6, the turbine and its disk 1 is placed so that its axis Y is horizontal and the root 3 of the blade 2 for mounting is inserted freely into the slot 4 situated in the bottom-most position. This is also shown in FIGS. 7 and 9. The blade is mounted in the disk via its steam outlet face, given that steam travels in the direction shown by arrow F.

Figure 8:
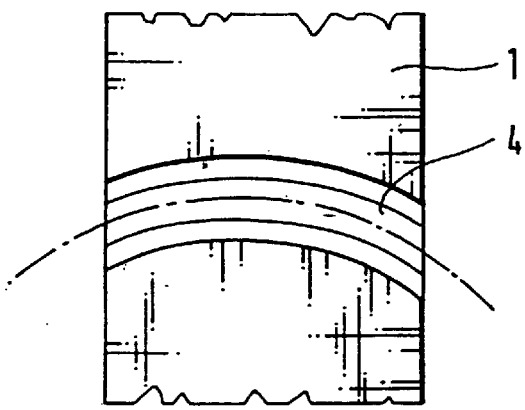
FIG. 8 is a view looking along arrow VIII of FIG. 7.
Figure 10:
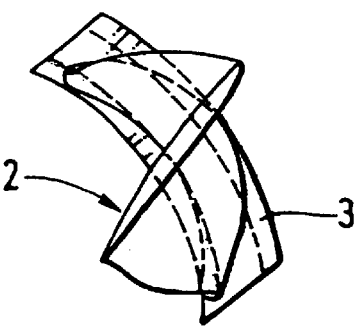
FIG. 10 shows the FIG. 9 blade seen along arrow X.

FIGS. 8 and 10 are views looking along arrows VIII and X of FIGS. 7 and 9 and show how the profiles of the slot 4 and of the Christmastree-shaped root 3 are curved.

Given the empty space H (FIG. 3) between the bottom of the slot 4 and the tip of the blade root 3, the root can slide freely in the slot 4 without any risk of the teeth of the Christmastree-shape jamming in the grooves of the slot, since the surface state of the teeth and of the grooves is carefully prepared.

Finally, the first stick 5 is inserted in the empty space between the end of the blade root 3 and the bottom of the slot 4 using a tool 10 as shown in FIG. 15. It suffices to strike the rear end of the tool in the direction of arrow $F_1$ with a mallet until the first stick comes to bear against the rim 8 on the blade root 3 (FIG. 13). The other two sticks are subsequently inserted in the same manner so as to come to bear against the preceding stick. Thereafter the disk is closed in conventional manner by means of the rings 9A and 9B (FIG. 14).

What is claimed is:

1. A turbine rotor disk fitted with blades having Christmastree-shaped roots, comprising:

at least one stick having a recessed portion; and a single, one-piece spring strip held in said recessed portion of said at least one stick, wherein said disk has slots which respectively receive said roots, said slots having a bottom portion such that said at least one stick and said spring strip are placed in each slot of said disk between said bottom portion and an end face of a root of a corresponding blade.

2. A rotor disk according to claim 1, wherein three of said sticks are disposed between the bottom of a slot in the disk and the end face of the root of the corresponding blade.

3. A rotor disk according to claim 1, wherein the end of the root of each blade has a rim against which one of said sticks comes into abutment.

4. A rotor disk according to claim 1, wherein said spring strip in any one of said sticks is a curved strip with the ends of the strip bearing in said recessed portion and with the curved central portion thereof bearing against the bottom of said slot of the rotor disk, the opposite face of the stick bearing against the end of the root of the blade.

5. A method of assembling a blade having a Christmastree-shaped root to a turbine rotor disk, the method comprising the following sequence of operations:

a) placing the rotor disk so that an axis of the rotor disk is in a horizontal position;

b) placing a slot of the disk in which the blade root is to be mounted in a bottom position;

c) installing the blade by slidably inserting the root of the blade into the slot of the disk; and d) fitting a single, one-piece spring strip into a recessed portion of a stick and then inserting the stick and spring strip into an empty space between a bottom of the slot in the disk and an end of the blade root until the inserted stick comes into abutment against a rim on the root of the blade.

6. An assembly method according to claim 5, wherein said sticks are inserted from the steam outlet side and the first stick to be inserted comes into abutment against said rim which is situated at the steam inlet side.

7. An assembly method according to claim 5, further including inserting additional sticks having respective recessed portions with spring strips into the empty space.

8. A rotor disk according to claim 1, wherein said Christmastree shaped roots have outwardly extending portions which decrease in width in a direction towards a corresponding stick.

* * * * *